(12) United States Patent
Heimbuch et al.

(10) Patent No.: US 6,395,743 B1
(45) Date of Patent: May 28, 2002

(54) HIV INTEGRASE INHIBITORS

(75) Inventors: Brian Heimbuch, North Brunswick; Sheo Singh, Edison; Deborah L. Zink, Manalapan; Magda Gagliardi, Monmouth Junction, all of NJ (US); Olga Genilloud; Ana Teran, both of Madrid (ES)

(73) Assignee: Merck & Co., Inc., Rahway, NJ (US)

( * ) Notice: Subject to any disclaimer, the term of this patent is extended or adjusted under 35 U.S.C. 154(b) by 6 days.

(21) Appl. No.: 09/689,174

(22) Filed: Oct. 12, 2000

Related U.S. Application Data

(60) Provisional application No. 60/159,347, filed on Oct. 13, 1999.

(51) Int. Cl.$^7$ ............ A61K 31/44; A61K 31/4015; A61K 31/4025; C07D 213/02; C07D 209/96
(52) U.S. Cl. ............ 514/278; 514/409; 548/407; 546/15; 435/76
(58) Field of Search ............ 548/407; 514/409, 514/278; 546/15

(56) References Cited

U.S. PATENT DOCUMENTS

| | | |
|---|---|---|
| 5,001,145 A | 3/1991 | Ramsay et al. |
| 5,045,457 A | 9/1991 | Banks et al. |
| 5,104,871 A | 4/1992 | Bell et al. |
| 5,171,742 A | 12/1992 | Meinke |

OTHER PUBLICATIONS

L. Ratner et al., "Complete Nucleotide sequence of the AIDS virus, HTLV–III", Nature, vol. 313, pp. 277–284 (Jan. 24, 1985).

H. Toh et al., "Close structural resemblance between putative polymerase of a Drosophila transposable genetic element 17.6 and pol gene product of Moloney murine leukaemia virus", The EMBO Journal, vol. 4, No. 5, pp. 1267–1272 (1985).

M. D. Power et al., "Nucleotide Sequence of SRV–1, Type D Simian Acquired Immune Deficiency Syndrome Retrovirus", Science, vol. 231, pp. 1567–1572 (1986).

L. H. Pearl et al., "A structural model for the retroviral proteases", Nature, vol. 329, pp. 351–354 (Sep. 24, 1987).

H. Zhao et al., "Hydrazide–Containing Inhibitors of HIV–1 Integrase" J. Med. Chem., vol. 40, pp. 937–941 (1997).

H. Zhao et al., "Arylamide Inhibitors of HIV–1 Integrase", J. Med. Chem., vol. 40, pp. 1186–1194 (1997).

R. L. LaFemina et al., "Inhibition of Human Immunodeficiency Virus Integrase by Bis–Catechols" Antimicrobial Agents & Chemotherapy, vol. 39, No. 2, pp. 320–324 (Feb. 1995).

*Primary Examiner*—Laura L. Stockton
(74) *Attorney, Agent, or Firm*—Kenneth R. Walton; Melvin Winokur

(57) ABSTRACT

Compounds useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines are described. Methods of treating AIDS and methods of preventing or treating infection by HIV are also described. The culture Actinoplanes sp. MA7220 (ATCC 202188) is also disclosed, as well as processes for making compounds of the present invention employing the culture.

10 Claims, 1 Drawing Sheet

HIV INTEGRASE INHIBITORS

CROSS-REFERENCE TO RELATED APPLICATIONS

This application claims the benefit of U.S. Provisional Application No. 60/159,347 filed Oct. 13, 1999, the disclosure of which is hereby incorporated by reference in its entirety.

FIELD OF THE INVENTION

The present invention relates to certain compounds, pharmaceutical compositions containing the compounds, and the microbial production of the compounds. The compounds are useful as HIV integrase inhibitors.

References are made throughout this application to various published documents in order to more fully describe the state of the art to which this invention pertains. The disclosures of these references are hereby incorporated by reference in their entireties.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame (Ratner et al., *Nature* 1985, 313: 277). Amino acid sequence homology provides evidence that the pol sequence encodes reverse transcriptase, integrase and an HIV protease (Toh et al., *EMBO J.* 1985, 4: 1267; Power et al., *Science* 1986, 231: 1567; Pearl et al., *Nature* 1987 329: 351). All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase and inhibitors of HIV replication. The applicants additionally demonstrate that inhibition of integrase in vitro and HIV replication in cells is a direct result of inhibiting the strand transfer reaction catalyzed by the recombinant integrase in vitro and integrase as a component of the preintegration complex in HIV infected cells. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Zhao et al. (*J. Med Chem.* 1997, 40: 937–941 and 1186–1194) describe hydrazide and arylamide HIV integrase inhibitors. Bis-catechols useful for inhibiting HIV integrase are described in LaFemina et al. (*Antimicrobial Agents & Chemotherapy* February 1995, 39:, 320–324).

SUMMARY OF THE INVENTION

Applicants have discovered that certain novel compounds are potent inhibitors of HIV integrase. These compounds are useful for the treatment of AIDS or HIV infections. More particularly, the present invention includes compounds of formula (I):

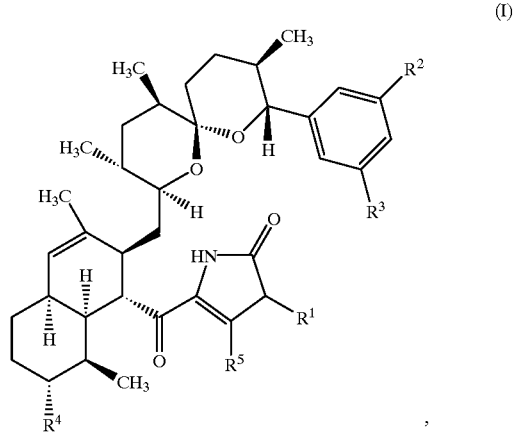

wherein
R$^1$ is —OH, —OCH$_3$, or

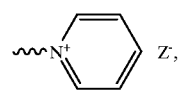

wherein Z$^-$ is a counterion; each of R$^2$, R$^3$, and R$^4$ is independently —OH or —OC(O)CH$_3$; and R$^5$ is (i) —OH when R$^1$ is —OH or —OCH$_3$ or (ii) —OC(O)CH$_3$ when R$^1$ is

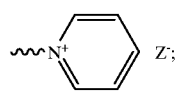

or a pharmaceutically acceptable salt thereof.
wherein
R$^1$ is —OH, —OCH$_3$, or

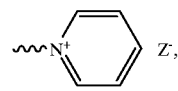

wherein Z$^-$ is a counterion; and each of R$^2$, R$^3$, and R$^4$ is independently —OH or —OC(O)CH$_3$; or a pharmaceutically acceptable salt thereof.

The present invention also includes use of these compounds in the inhibition of HIV integrase, the prevention of infection by HIV, the treatment of infection by HIV, and the treatment of AIDS and/or ARC, wherein the compounds are used per se or as their pharmaceutically acceptable salts or hydrates (when appropriate), either alone or as ingredients in pharmaceutical compositions, optionally in combination with other antivirals, anti-infectives, immunomodulators, antibiotics or vaccines. The present invention further includes the culture Actinoplanes sp. MA7220 (ATCC 202188) and processes for making compounds of the present invention employing the culture.

These and other embodiments, aspects and features of the present invention are either further described in or will be apparent from the ensuing description, examples, and appended claims.

DETALED DESCRIPTION OF THE INVENTION

Figure 1:
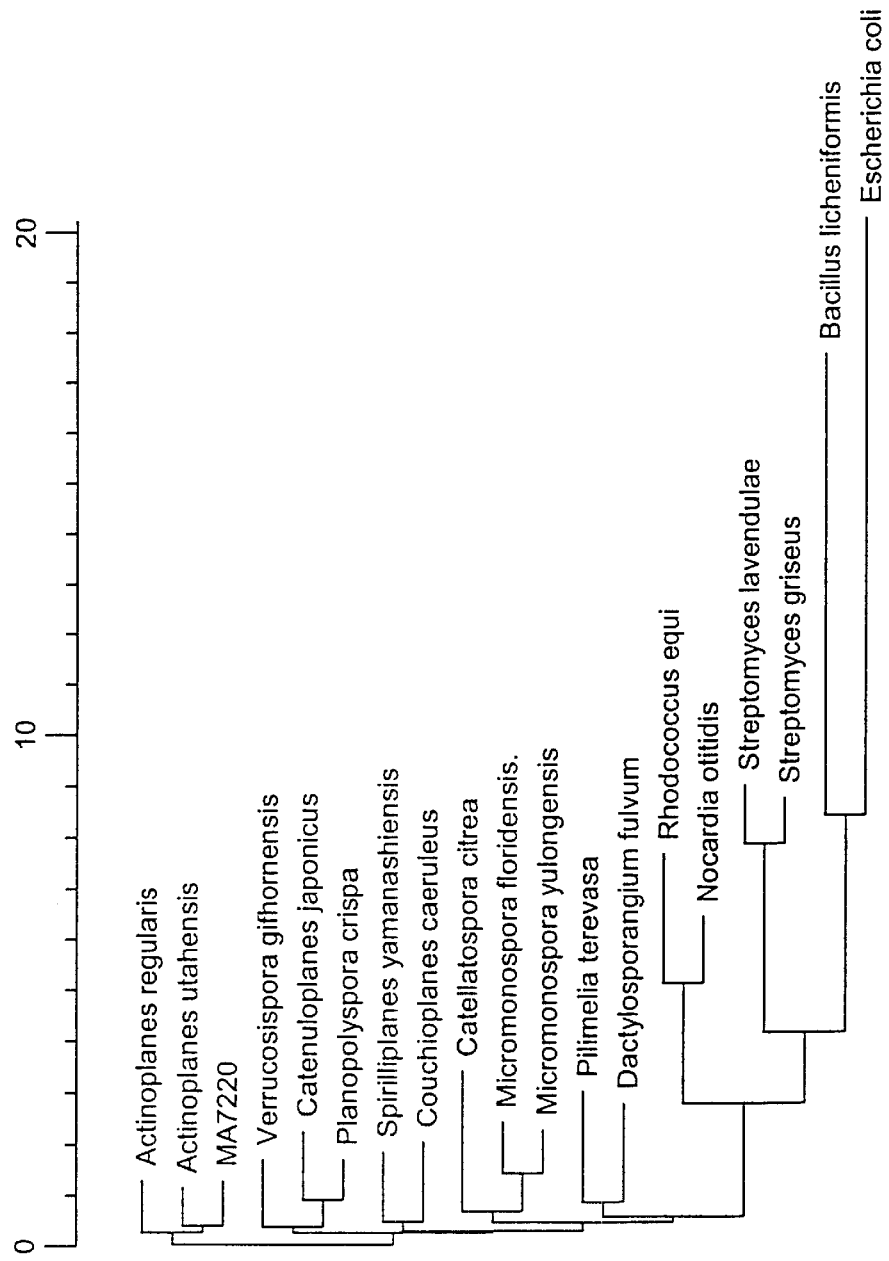
FIG. 1 presents a Neighbor Joining clustering analysis of the 16s rRNA sequence of MA 7220 to 16s rRNA sequences of known organisms.

The present invention includes compounds of Formula (I) as described above. These compounds and their pharmaceutically acceptable salts are useful as HIV integrase inhibitors. In one embodiment, the compound is

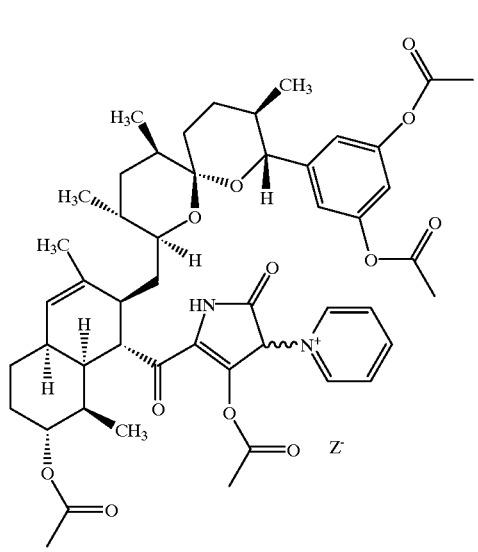

(a)

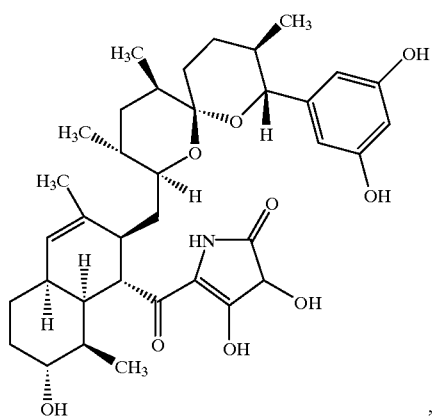

(b)

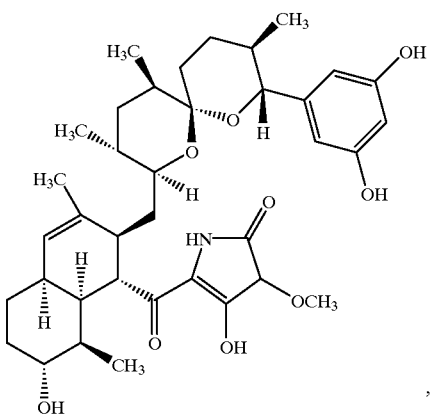

(c)

or (d) a pharmaceutically acceptable salt of (a), (b) or (c).

In an aspect of the foregoing embodiment, the compound is

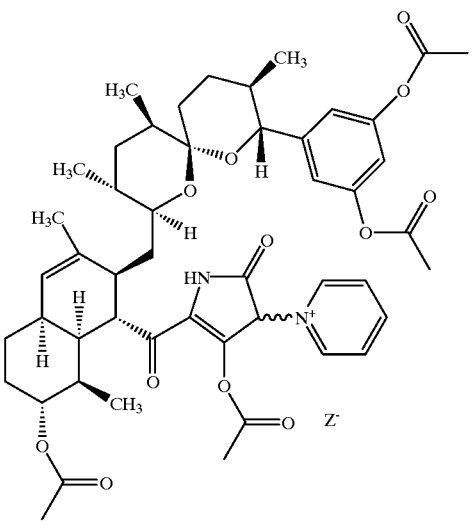

or a pharmaceutically acceptable salt thereof. The counterion $Z^-$ is any organic or inorganic anion that will balance the charge on the pyridinium cation. Suitable counterions include, but are not limited to, the anions set forth below in the description of pharmaceutically acceptable salts. Exemplary anions are chloride, bromide, trifluoroacetate, mesylate, and acetate.

In another aspect of the preceding embodiment the compound is

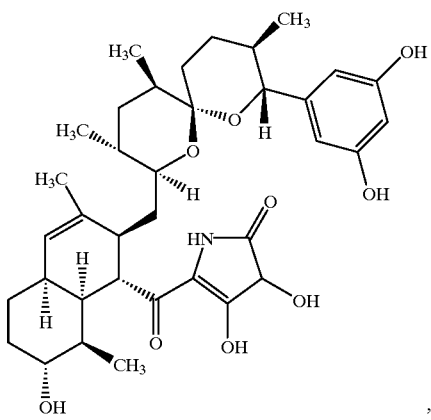

or is a pharmaceutically acceptable salt thereof.

In still another aspect of aspect of the preceding embodiment, the compound is

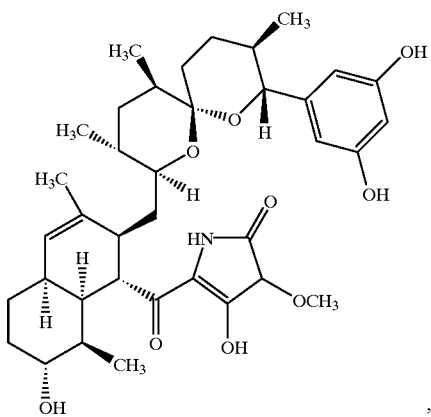

or a pharmaceutically acceptable salt thereof.

The present invention also includes pharmaceutical compositions which comprise a therapeutically effective amount of a compound of the present invention and a pharmaceutically acceptable carrier. These pharmaceutical compositions are useful for inhibiting HIV integrase, for treating infection by HIV, or for treating AIDS or ARC. In one embodiment, the pharmaceutical compositions further comprise a therapeutically effective amount of an AIDS treatment agent selected from (a) an AIDS antiviral agent, (b) an immunomodulator, and (c) an anti-infective agent (all described below). A class of this embodiment is the pharmaceutical compositions which include an AIDS treatment agent, such as indinavir or a pharmaceutically acceptable salt thereof.

The present invention also includes pharmaceutical compositions which comprise a combination of a therapeutically effective amount of a compound of Formula (I) and a therapeutically effective amount of an AIDS treatment agent selected from (a) an AIDS antiviral agent, (b) an immunomodulator, and (c) an anti-infective agent.

The present invention also includes pharmaceutical compositions made by combining the compound of Formula (I) and a pharmaceutically acceptable carrier. The present invention also includes a process for making pharmaceutical compositions which comprises combining a compound of Formula (I) and a pharmaceutically acceptable carrier.

The present invention also includes methods of inhibiting HIV integrase, of treating infection by HIV, and of treating AIDS or ARC, wherein the methods comprise administering to a mammal in need of such inhibition or treatment a therapeutically effective amount of a compound of Formula (I), optionally in combination with a therapeutically effective amount of another AIDS treatment agent selected from selected from (a) an AIDS antiviral agent (e.g., indinavir or one of its pharmaceutically acceptable salts), (b) an immunomodulator, and (c) an anti-infective agent. Also included in the present invention are methods of inhibiting HIV integrase, of treating infection by HIV, and of treating AIDS or ARC, by administering to a mammal in need thereof one of the pharmaceutical compositions as heretofore described.

The present invention also includes a culture of Actinoplanes sp. MA7220 (ATCC 202188), which can be used to form compounds of Formula (II):

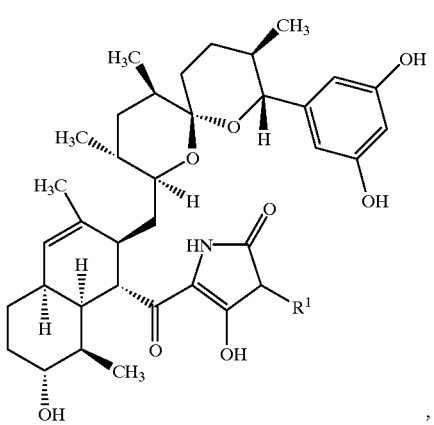

(II)

wherein $R^1$ is —OH or —OCH$_3$. Compounds of Formula (II) may be isolated from the aerobic fermentation of a culture of MA7220 (ATCC 202188). A culture of MA7220 (ATCC 202188) is defined as substantially free of its natural soil contaminants and capable of forming a compound of Formula (II) in a recoverable amount. The culture should be free from viable contaminating microorganisms deleterious to the production of a compound of Formula (II). A biologically pure culture of MA7220 (ATCC 202188) may also be employed. In one embodiment, the present invention includes a culture of MA 7220 (optionally biologically pure), or a mutant thereof, capable of producing in a recoverable amount a compound of Formula (II).

Suitable mutant strains of MA7220 can be obtained by chemically induced mutagenesis using mutagens such as nitrosoguanidine, 1-methyl-3-nitro-1-nitrosoguanidine, ethyl methane sulfonate, 2-aminopurine, and the like. Mutant strains can also be obtained by radiation-induced mutagenesis, such as by irradiation with ultraviolet light (e.g., using a germicidal lamp), X-rays, or gamma rays (e.g., using a cobalt-60 source). Recombinant DNA techniques such as protoplast fusion, plasmid incorporation, gene transfer and the like may also be employed. Further description of mutagenic technqiues can be found in Vinci and Bing, "Strain Improvement by Nonrecombinant Methods", in *Manual of Industrial Microbiology and Biotechnology* 1999, 2d edition, edited by Demain et al., ASM Press, 103–113; and in Carlton and Brown, "Gene Mutation", Chapter 13 in *Manual of Methods for General Bacteriology* 1985, edited by Gerhardt et al., ASM Press, 222–229.

The present invention also includes a process for making a compound of Formula (II), which comprises cultivating Actinoplanes sp. MA7220 (ATCC 202188) or a mutant thereof under conditions suitable for formation of the compound and recovering the compound. In one aspect the process comprises:

(a) fermenting a culture of Actinoplanes sp. MA7220 (ATCC 202188) or a mutant thereof to produce a fermentation broth;

(b) extracting the fermentation broth with an organic solvent; and (c) isolating the compounds of Formula (II).

The compounds of Formula (II) are suitably isolated by partitioning the fermentation extract between the organic solvent and water, followed by size exclusion chromatography and normal or reverse-phase chromatography.

The present invention also includes the use of a compound of Formula (I) or a pharmaceutical composition (as described above) including said compound in the preparation of a medicament for (a) inhibiting HIV integrase, (b) treating infection by HIV, or (c) treating AIDS or ARC.

The compounds of the present invention may have asymmetric centers and may occur, except when specifically noted, as mixtures of stereoisomers or as individual diastereomers, or enantiomers, with all isomeric forms being included in the present invention.

The definitions of each of the variables (e.g., $R^1$ and $R^2$) in Formula (I) are completely independent of each other. If any variable occurs more than one time in any constituent, its definition on each occurrence is independent of its definition at every other occurrence. Combinations of substituents and/or variables are permissible only if such combinations result in stable compounds.

As can be recognized by one of ordinary skill in the art, the compounds of the present invention can exist as tautomers, and thus it is understood that the present invention includes tautomeric forms (individually and in mixtures) of the compounds of the invention. For example, it is understood that a compound of Formula (I) includes, but is not limited to, tautomeric forms IA to IF as follows:

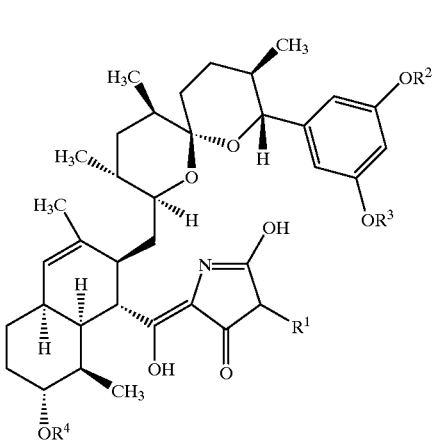

(IA)

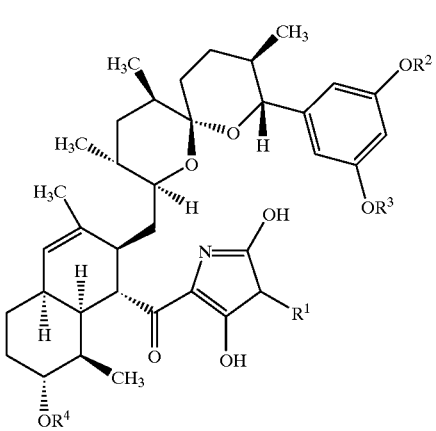

(IB)

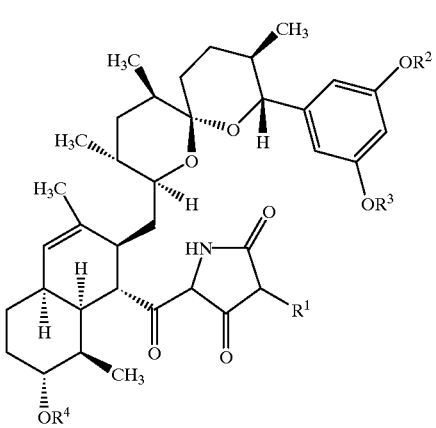

(IC)

-continued

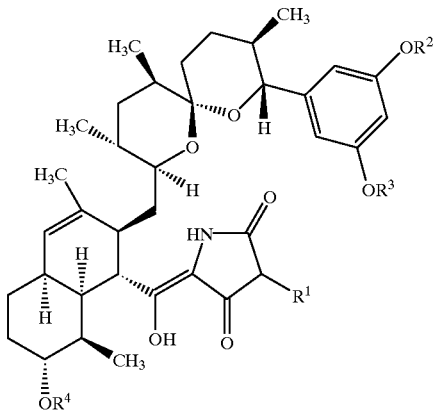

(ID)

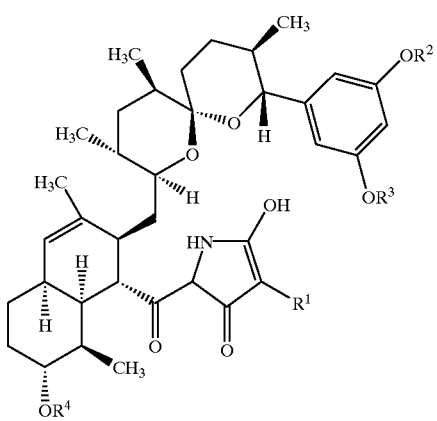

(IE)

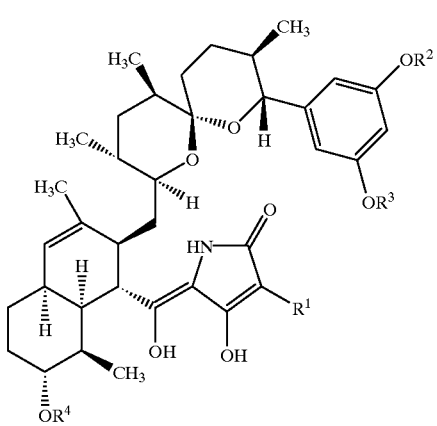

(IF)

By naming or referring to compound (I), it is understood for the purposes of the present application that tautomers (IA) to (IF) are included, individually or in combination.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" (defined below) shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs* 1985, edited by H. Bundgaard, Elsevier. The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

The present invention also provides for the use of a compound of Formula (I) to make a pharmaceutical composition useful for inhibiting HIV integrase and in the treatment of AIDS or ARC.

Applicants have discovered that compounds of Formula (I), are useful for inhibiting HIV integrase. The compounds of Formula (I) are prepared by an aerobic fermentation procedure employing MA 7220, as described below. The compounds of Formula (I) can also be prepared by analogous fermentation procedures using mutants of MA 7220.

ATCC Deposit of MA7220 (ATCC 202188),
Identified as Actinoplanes sp.

A sample of MA7220 (ATCC 202188) was deposited at the American Type Culture Collection (ATCC), 10801 University Boulevard, Manassas, Va. 20110–2209 on Jan. 13, 1999. The culture access designation is 202188. This deposit will be maintained in the ATCC for at least 30 years and will be made available to the public upon the grant of a patent disclosing it. It is understood that the availability of a deposit does not constitute a license to practice the subject invention in derogation of patent rights granted by government action.

General Characteristics and Description of MA7220
(ATCC 202188)

MA 7220 can be generally characterized as set forth below, wherein (1) observations of growth and general cultural characteristics were made in accordance with the methods of Shirling and Gottleib, Int. *J. System. Bacteriol.* 1966, 16: 313–340; (2) chemical composition of the cells was determined using the methods of Lechevalier and Lechevalier, in *Actinomycete Taxonomy* 1980, edited by A. Dietz and D. W. Thayer, Society for Industrial Microbiology, Arlington, Va., 225–291; and (3) 16s rRNA analysis was done using standard conditions as described in Table 1.

Isolation conditions—Culture MA7220 was isolated from a desert soil sample collected in Kingman, Ariz. The soil sample was flooded with tap water, baited with dog hairs and incubated for four weeks at 28° C. The isolation medium was Soil Extract Agar containing dog hairs.

Analysis of Whole Cell Extracts—Peptidoglycan contains meso-diaminopimelic acid. Whole cell sugars contain xylose and ribose.

Colony Morphology—Good growth was observed on SNY Agar and Czapeks Agar (available commercially from Difco, Detroit, Mich. USA) with 0.2% yeast extract. SNY Agar (pH=7) consists of sodium nitrate (1 g), magnesium sulfate (0.1 g), sucrose (10 g), and agar (15 g), to which is added after autoclaving 1M potassium phosphate 7.0 buffer (2 mL), 2× trace salts solution (=calcium chloride (4 g), manganese sulfate (2 g), ferrous sulfate (1 g), zinc sulfate (0.05 g), 0.1N HCl (1 L), yeast extract (0.5 g). Substrate mycelium is orange on SNY Agar and Czapeks Agar with yeast extract, incubated at 27° C. No aerial mycelium is present. Colonies were opaque, raised with an entire edge and matte surface.

Micromorphology—Substrate mycelium is 0.57 µm; no aerial mycelium was present. Sporangia present on the substrate mycelium after four weeks of incubation on SNY Agar at 27° C., were 3.42–6.3 µm in diameter.

16s-rRNA Analysis—1376 bases corresponding to *E. coli* 16s rRNA positions 18–1421 were sequenced. A clustering analysis of the 16s rRNA sequence of MA 7220 to 16s rRNA sequences of known organisms was done using the Neighbor Joining method, which is described in Saitou et al., *Mol. Biol. Evol.* 1987, 4: 406–425. The results of the analysis are shown in FIG. 1.

TABLE 1

Method for 16s rRNA analysis of MA7220

| Sequencing steps | Method |
| --- | --- |
| Prepare DNA from MA 7220 | MA7220 was grown in liquid SNY media for 7 days. Cells were harvested then subjected to a DNA isolation kit (K1800-01) provided by Invitrogen (1600 Faraday Ave. Carlsbad, CA USA 92008). |
| PCR Amplify DNA | Amplification was carried out with primers (concentration 5 pmol/reaction)16s 27f and 16s 1392r (8) using "Ready to Go PCR beads" provided by Amersahmpharmacia Biotech (800 Centennial Ave, PO Box 1327 Piscataway, NJ USA 08855). Amplification conditions were 30 cycles of 1 min 94° C.; 1 min 55° C.; and 2 min 72° C. Finally there was an extension step of 8 min at 72° C. |
| Cloning of DNA Fragments and Plasmid purification | Amplified PCR fragments were cloned into plasmid vectors using the TOPO cloning Kit (K4500-1) provided by Invitrogen. Plasmids were purified using the Mini prep kit (K1900-01) supplied by Invitrogen. |
| Sequencing | Approximately 1370 bases of the 3' end of the fragment was sequenced using an ABI Prism Big Dye Terminator Cycle Sequencing Kit from PE Applied Biosystems (850 Lincoln Centre Drive, Foster City, CA USA 94404). |
| Analysis of Sequence | Sequence data for MA7220 was aligned and analyzed using software package "Gene Base" supplied by Applied Maths (Risquons-Toutstraat 38, 8511 Kortrijk, Belgium). Neighbor Joining analysis was done to create similarity matrix and a dendrogram. Reference sequences for comparison to the MA7220 sequence were obtained from The National Center for Biotechnology Information (National Library of Medicine Building 38A, Room 8N805, Bethesda, MD 20894; URL--http://www.ncbi.nlm.nih.gov/). The Accession number for the reference sequences are as follows: *Rhodococcus equi* - M29574, *Nocardia otitidis* - X80611, *Catenuloplanes japonicus* - D85476, *Planopolyspora crispa* - AB024701, *Verrucosispora gifhornensis* - Y15523, *Actinoplanes regularis* - X93188, *Actinoplanes utahensis* - X80823, *Spirilliplanes yamanashiensis* - D63912, *Couchioplanes caeruleus* - D85478, *Micromonospora floridensis* - X92621, *Micromonospora yulongensis* - X92626, *Pilimelia terevasa* - D86946, *Dactylosporangium fulvum* - X93192, *Catellatospora citrea* - D85477, *Streptomyces lavendulae* - D85112, *Streptomyces griseus* - Y15501, *Bacillus licheniformis* - D31739, *Escherichia coli* - AE000474 |

The 16s rRNA clustering analysis indicates that MA7220 belongs to the genus Actinoplanes. The general description, both colony morphology and micro morphology is consistent with the genus Actinoplanes (see Vobis in *Bergey's Manual of Systematic Bacteriology* 1989, 4, edited by St. Williams, Sharpe and Holt, Williams and Wilkins, Baltimore; Yokota et al., *Int. J. Bacteriol.* 1993, 43: 805–812; Tamura et al., *Int. J. Bacteriol.* 1994, 44: 193–203; and Rheims et al., *Int. J. Bacteriol.* 1998, 48: 1119–27). However, it is reported by Vobis (cited in preceding sentence) that genra of the family Micromonosporaceae have a Type II cell wall (cell walls contain meso-diaminopimelic acid and major amounts of arabinose and xylose). Whole cell hydrolysates of MA 7220 contain meso-diaminopimelic acid and xylose but not arabinose. Since the publication by Vobis, there have been reports in the literature citing that genra of the Micromonosporaceae family are more diverse in their cell wall composition than originally reported of strains being classified in the genus Actinoplanes that do not contain major amounts of both arabinose and xylose (Yokota et al. 1993, Tamura et al. 1994, and Rheims et al. 1998, cited above). Accordingly, based on the data presented herein, MA7220 should be classified and identified as a species in the genus Actinoplanes.

In general, MA7220 (ATCC 202188) is strain cultured on a solid medium, or in an aqueous nutrient medium containing sources of assimilable carbon and nitrogen. For example, the cultures can be grown under submerged aerobic conditions (e.g., shaking culture, submerged culture, etc.) The aqueous medium is preferably maintained at a pH in the range of from about 6 to about 8 at the initiation of the fermentation process. The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred source of carbon in the nutrient medium are carbohydrates such as glucose, xylose, galactose, glycerin, starch, sucrose, dextrin, and the like. Other sources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultural conditions is one method of culturing the cells. For production in small amounts, a shaking or surface culture in a flask or bottle is employed. When the growth is carried out in large tanks, vegetative forms of the organism for inoculation in the production tanks may be employed in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to be in the range of from about 6 to about 7 to the autoclaving step.

Agitation and aeration of the culture mixture may be accomplished in a variety of ways. Agitation may be provided by a propeller or similar mechanical agitation equipment, by revolving or shaking the fermentor or growth flask, by various pumping equipment, or by the passage of sterile air through the medium. Aeration may be effected by passing sterile air through the fermentation mixture.

The fermentation is typically conducted at a temperature in the range of from about 25 to about 30° C. (e.g., about 28° C.) for a period of from about 8 to about 12 days, which may be varied according to fermentation conditions and scales.

Preferred culturing/production media for carrying out the fermentation those set forth in the Examples.

After growth is completed, the cells are harvested by adding the appropriate solvent, e.g. methyl ethyl ketone, to the entire culture medium and cells. If the culture is grown in a liquid fermentation, the growth could be harvested by other conventional methods, e.g., centrifugation and filtration, and then extracted with the appropriate solvent, e.g., methyl ethyl ketone.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methyl ethyl ketone, followed by filtration of the extract through filtering aid such as diatomaceous earth. The methyl ethyl ketone layer of the filtrate is separated and concentrated to dryness initially by evaporating under reduced pressure followed by lyophilization. The compounds are finally isolated either by solvent partitioning and crystallization or by preparative HPLC on reversed phase systems.

Compounds of Formula (I) may be isolated from the aerobic fermentation of a culture of MA7220 (ATCC 202188). A culture of MA7220 (ATCC 202188) is defined as substantially free of its natural soil contaminants and capable of forming compounds of Formula (I) in recoverable amounts. The culture employed in the present invention should be free from viable contaminating microorganisms deleterious to the production of the compound of Formula (I). A biologically pure culture of MA7220 (ATCC 202188) may also be employed.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, trifluoroacetate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a compound of the invention each mean providing the compound or a prodrug of the compound to the subject in need of treatment. When a compound of the invention or prodrug thereof is provided in combination with one or more other active agents (e.g., AIDS antivirals), "administration" and its variants are each understood to include concurrent and sequential provision of the compound or prodrug thereof and other agents.

The term "subject," (alternatively referred to herein as "patient") as used herein refers to an animal, typically a mammal, preferably a human, who has been the object of treatment, observation or experiment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results directly, or indirectly, from combination of the specified ingredients in the specified amounts.

By "pharmaceutically acceptable" it is meant the carrier, diluent or excipient must be compatible with the other ingredients of the formulation and not deleterious to the recipient thereof.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of about 0.01 to about 1000 mg/kg body weight in divided doses. One preferred dosage range is from about 0.1 to about 200 mg/kg body weight orally in divided doses. Another preferred dosage range is from about 0.5 to about 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase inhibitor) |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL, HIV positive, AIDS |
| Alpha Interferon | Glaxo Wellcome | Kaposi's sarcoma, HIV, in combination w/Retrovir |

-continued

ANTIVIRALS

| Drug Name | Manufacturer | Indication |
|---|---|---|
| Ansamycin LM 427 | Adria Laboratories Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (-) 6-Chloro-4(S)-cyclopropylethynyl-4(S)-trifluoromethyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound Q | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |
| ABT-378 | Abbott | HIV infection, AIDS, ARC (protease inhibitor) |
| JE2147/ AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| BMS 232632 | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or sequential treatments of a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. The preparations of ddC, ddI and AZT are described in EP 484071. A preferred inhibitor of HIV protease is the sulfate salt of indinavir, which is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Still another preferred protease inhibitor is Compound Q, which is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido) piperazinyl))pentaneamide, preferably administered as the sulfate salt. Compound Q can be prepared as described in U.S. Pat. No. 5,646,148. Preferred non-nucleoside inhibitors of HIV reverse transcriptase include efavirenz, which can be prepared as described in U.S. Pat. No. 5,519,021. These combinations may have unexpected effects on limiting the spread and degree of infection of HIV. Preferred combinations include a compound of the present invention with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and amprenavir and abacavir; (5) zidovudine and lamivudine.

Another preferred combination is a compound of the present invention with indinavir and Compound Q and optionally with one or more of efavirenz, AZT, 3TC, ddI and ddC. In one embodiment of this combination, the weight ratio of indinavir to Compound Q is from about 1:1 to about 1:2, wherein the amount of indinavir employed is in the range of from about 200 to about 1000 mg. Indinavir and Compound Q can be administered concurrently or sequentially in either order from one to three times per day.

In such combinations the compound of the present invention and other active agents may be administered together or separately. In addition, the administration of one agent may be prior to, concurrent to, or subsequent to the administration of other agent(s).

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Abbreviations used in this specification include the following:

Ac=acetyl
AIDS=acquired immune deficiency syndrome
ARC=AIDS related complex
ESIMS=electron spray ionization mass spectroscopy
FABMS=fast atom bombardment mass spectroscopy
ATCC=American Type Culture Collection
FVM=frozen vegetative mycelia
HIV=human immunodeficiency virus
HPLC=high performance liquid chromatography
HR-EI MS=high resolution electron impact mass spectroscopy
Me=methyl
MEK=methyl ethyl ketone
NMR=nuclear magnetic resonance
SNY=sucrose nitrate yeast
TFA=trifluoroacetic acid
UV=ultraviolet The following examples serve only to illustrate the invention and its practice. The examples are not to be construed as limitations on the scope or spirit of the invention.

EXAMPLE 1

Fermentation of MA7220 (ATCC 202188)

A. Media

Nutrient A contained the following in g/L of distilled water: yeast extract (1 g), beef extract (1 g), casein hydrolysate (2 g), glucose (10 g), and agar (15 g), which was adjusted to a pH of 7.2 with NaOH.

Seed medium contained the following in g/L of distilled water: soluble starch (20 g), dextrose (10 g), NZ-amine type E (Sheffield) (5 g), beef extract (Difco) (3 g), Bacto peptone (Difco) (5 g), yeast extract (Fidco) (5 g), and calcium carbonate (1 g). The pH was adjusted to 7 with NaOH prior to adding calcium carbonate.

Production medium contained the following in g/L of water: dextrin (20 g), B-cyclodextrin (10 g), primary yeast (10 g), tomato paste (20 g), and $CoCl_2.6H_2O$ (0.005 g). The pH was adjusted to 7.2 with NaOH.

B. Inoculum Preparation

FVM supported on nutrient medium agar plugs were spread over Nutrient A agar plates, which were incubated at 28° C. for 7 to 10 days. The resulting growth was used to inoculate SNY slants.

C. Seed Culture

A seed culture was prepared by inoculating 50 mL of seed medium in a 250 mL triple baffled flask with all of the growth from one SNY slant, wherein the growth was removed by scraping the slant's surface, and incubating the inoculated flask at 28° C. with shaking at 220 rpm for about 96 hours.

D. Production Culture and Extraction 2 mL of seed culture was aseptically transferred to each of several 250 mL non-baffled flasks containing 46 mL of production medium and the flasks were incubated at 28° C. with shaking at 220 rpm for 8 days. The resulting production culture was worked up as described in Example 2.

EXAMPLE 2

Isolation of Compounds A and B

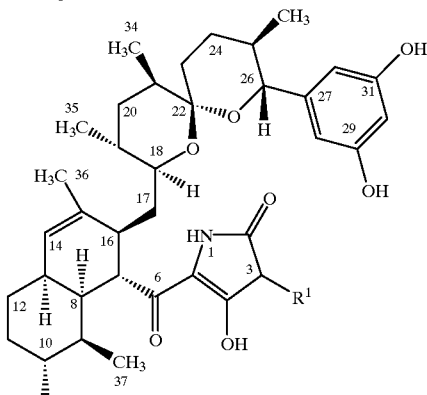

Compound A: $R^1$ = OH
Compound B: $R^1$ = $OCH_3$

Two liters of the production culture produced as described in Example 1 (pH=5.9) was extracted with 2.1 L of MEK. The layers were separated, and the MEK layer was concentrated under reduced pressure. The residual water was removed by lyophilization to give a yellow powder that was triturated with 100 mL of methanol and filtered. Ninety five mL of this solution was chromatographed on to a 2.0 L column of SEPHADEX LH20. Elution of the column with methanol eluted the activity in a broad band from 1000 to 2000 mL of the elution volume. Fractions were combined and concentrated to give the combined active fraction as a yellow solid. An aliquot (108 mg) of this fraction was chromatographed on ZORBAX RX C-8 (22×250 mm), a reverse phase HPLC column. The column was eluted at 8 mL/min with a 60 minutes gradient of 20 to 50% aqueous acetonitrile containing 0.05% TFA followed by isocratic elution with 50% aqueous acetonitrile. The activity eluted in two zones. Lyophilization of the first active zone fractions eluting from 70–76 minutes and the second active zone fractions eluting from 83–88 minutes gave Compound A and Compound B, respectively, as colorless powders. These compounds eluted at $t_R$=12.9 and 17.4 minutes, respectively, in analytical HPLC (ZORBAX RX C-8, 4.6×250 mm, 50% aqueous acetonitrile +0.1% TFA, 1 mL/min).

Compound A: UV ($CH_3CN$—$H_2O$+0.1% TFA): 220, 285 nm, ESIMS (m/z): 640 $(M+H)^+$, 638 $(M-H)^-$; Scanning HR-EI data was obtained on the hexa-TMS (trimethly silyl derivative) characteristic fragment ions were observed at: m/z 695.4341=479.3155+3×$C_3H_8Si$ (calcd for $C_{31}H_{43}O_4$+3×$C_3H_8Si$: 479.3161+216.1186); 605.3663=461.2872+2×$C_3H_8Si$ (calcd for $C_{26}H_{39}NO_6$+2×$C_3H_8Si$): 461.2777+144.0791); 449.2542=305.1751+2×$C_3H_8Si$ (calcd for $C_{18}H_{25}O_4$+2×$C_3H_8Si$: 305.1752+144.0791), 358.1342=142.0155+3×$C_3H_8Si$ (calcd for $C_5H_4NO_{4+}$3×$C_3H_8Si$; 142.0140+216.1186). $^{13}$C NMR (acetone-$d_6$) δ: 194.3, 192.2, 176.4, 159.1 (2C), 145.2, 136.6, 127.6, 107.0 (2C), 102.9, 102.6, 98.7, 81.0, 78.9, 74.5, 70.7, 45.9, 43.1, 43.0, 42.9, 40.8, 39.9, 39.8, 37.3, 37.2, 35.5, 33.9, 30.9, 30.2, 29.2, 22.7, 18.6, 18.5, 16.8, 15.3. See Table 1 for complete $^1$H and $^{13}$C NMR assignments in $C_5D_5N$.

Compound B: UV ($CH_3CN$—$H_2O$+0.1% TFA): 220, 285 nm, ESIMS (m/z): 653 $(M+H)^+$; $^{13}$C NMR (acetone-$d_6$) δ: 192.8, 192.5, 176.9, 159.1 (2C), 145.2, 136.5, 127.5, 107.0 (2C), 103.5, 102.6, 98.7, 86.6, 79.9, 74.5, 70.7, 53.5, 45.8, 43.3, 43.0, 42.9, 40.8, 40.1, 39.8, 37.4, 37.3, 35.5, 33.9, 31.0, 30.9, 29.2, 22.7, 18.6, 18.5, 16.8, 15.3. Most of the upfield signals from 15–86 ppm were split due to isomeric equilibrium at C-3. $^1$H NMR spectrum of this compound was virtually identical to Compound A, therefore, only additional and/or shifts with significant changes are listed. $^1$H NMR (acetone-$d_6$) δ: 5.00 (1H, s, H-3), 3.38 (3H, s, 3—$OCH_3$).

TABLE 1

$^1$H and $^{13}$C NMR Assignment of Compound A in $C_5D_5N$

| Position | δC | δH | Position | δC | δH |
|---|---|---|---|---|---|
| 2 | 177.08 | — | 20 | 35.41 | 1.98, m; 1.05, m |
| 3 | 81.78 | 5.84, brs | 21 | 37.19 | 1.75, m |
| 4 | 196.27 | — | 22 | 98.71 | — |
| 5 | 103.34 | — | 23 | 33.90 | 2.05, m; 1.39, m |
| 6 | 192.27 | — | 24 | 29.29 | 2.05, m; 1.70, m |
| 7 | 43.28 | 4.36, dd, 12.5, 9.6 | 25 | 37.19 | 1.75, m |
| 8 | 42.72 | 2.58, td, 4, 12.4 | 26 | 80.09 | 4.41, d, 10 |
| 9 | 46.16 | 1.95, m | 27 | 145.55 | — |
| 10 | 70.63 | 4.24, dt, 10, 4 | 28 | 107.41 | 7.04, d, 2 |
| 11 | 37.79 | 2.31, m; 1.60, m | 29 | 160.38 | — |
| 12 | 30.35 | 1.75, m; 1.50, m | 30 | 103.61 | 6.94, t, 2 |
| 13 | 39.82 | 2.10, m | 31 | 160.38 | — |
| 14 | 127.60 | 5.50, brd, 6 | 32 | 107.41 | 7.04, d, 2 |
| 15 | 136.36 | — | 33 | 18.83 | 0.89, d, 6.4 |
| 16 | 40.79 | 3.07, brt, 7.2 | 34 | 15.47 | 0.95, d, 7.2 |
| 17 | 39.99 | 1.95, m; 1.85, m | 35 | 18.37 | 0.56, d, 6.4 |
| 18 | 74.49 | 3.50, t, 7.2 | 36 | 23.03 | 1.83, d, 1.5 |
| 19 | 30.88 | 1.29, m | 37 | 17.50 | 138, d, 7.2 |

EXAMPLE 3

Acetylation and Amination of Compound A

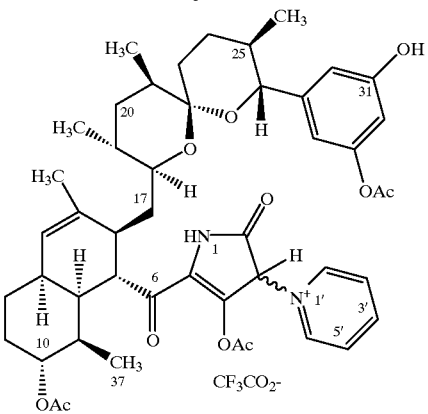

Compound C, isomer A
Compound D, isomer B

Acetic anhydride (0.4 mL) was added to a 0.5 mL pyridine solution of 80 mg semi-purified sample of Compound A. The solution was stirred overnight at room temperature, quenched by addition of 1 mL methanol and concentrated to dryness under reduced pressure. Reverse phase analytical HPLC (ZORBAX RX C-8, 4.6×250 mm, 80% aqueous acetonitrile containing 0.1% TFA, flow rate=1 mL/min) indicated formation of two major products, $t_R$=6.77 minutes and $t_R$=9.08 minutes in the ratio of 2:3, respectively.

These compounds were purified by preparative reverse phase HPLC using ZORBAX RX C-8 (22×250 mm) column. Gradient elution at 8 mL/min with 50 to 80% aqueous acetonitrile +0.1% TFA over 60 minutes eluted first compound in between 49–52 minutes and the second compound in between 57–62 minutes. Lyophilization of fractions gave Compound C (isomer A) and Compound D (isomer B)), both as amorphous powders.

Compound C: UV (CH$_3$CN—H$_2$O+0.1% TFA): 260, 280 nm; ESIMS (m/z): 869 (M+H)$^+$; HRFABMS (m/z): 869.4223, M+H (calcd for C$_{49}$H$_{60}$N$_2$O$_{12}$+H: 869.4224). $^{13}$C NMR (CD$_3$CN) δ: 200.20, 181.92, 172.5 (br), 171.2 (br), 170.71 (2C), 152.18 (2C), 147.94, 146.43, 142.82 (2C), 139.17, 129.49 (2C), 126.62, 120.1 (2C), 116.0, 102.5, 99.2, 79.8, 78.8, 75.4, 74.4, 44.9, 44.5, 44.1, 40.9, 37.9, 37.4 (2C), 35.6, 34.7, 33.5, 31.6, 30.9, 28.9, 25.6, 23.3, 21.7, 21.6 (2C), 19.7, 18.5 (2C), 18.0, 15.7.

Compound D: UV (CH$_3$CN—H$_2$O+0.1% TFA): 260, 280 nm; ESIMS (m/z): 869 (M+H)$^+$; HRFABMS (m/z): 869.4218, M+H (calcd for C$_{49}$H$_{60}$N$_2$O$_{12}$+H: 869.4224); $^{13}$C NMR (CD$_3$CN) δ: 200.0, 181.8, 172.2 (2C), 171.1, 170.7, 152.0 (2C), 147.9, 146.4, 141.8 (2C), 139.4, 129.2(2C), 126.1, 120.7(2C), 116.0, 102.5, 99.0, 79.4, 78.5, 74.9, 73.8, 45.4, 44.5 (2C), 41.4, 37.4 (2C), 35.4, 34.9 (2C), 33.7, 32.1, 30.5, 28.8, 25.4, 23.2, 21.9, 21.6 (2C), 19.8, 18.4 (2C), 17.4, 15.6. Both compounds showed a number of broad signals due to slow isomeric equilibration at C-3

EXAMPLE 4

HIV Integrase Assay: Strand Transfer Catalyzed by Recombinant Integrase and Preintegration Complexes Assays for the strand transfer activity of integrase were conducted according to Wolfe et al., *J. Virol.* 1996, 70: 1424 and Farnet and Bushman, *Cell* 1997, 88: 483 for recombinant integrase and preintegration complexes, respectively, hereby incorporated by reference. Representative compounds tested in the integrase assay demonstrated IC50's of 1 micromolar or less. Further, representative compounds tested in the preintegration complex assay also demonstrated IC50's of 1 micromolar or less.

EXAMPLE 5

Assay for Inhibition of HIV Replication

Assays for the inhibition of acute HIV infection of T-lymphoid cells were conducted according to Vacca et al., *Proc. Natl. Acad. Sci. USA* 1994, 91: 4906, herein incorporated by reference. Representative compounds tested in the present assay demonstrated IC$_{95}$'s of 10 micromolar or less.

EXAMPLE 6

Oral Composition

As a specific embodiment of an oral composition of a compound of this invention, 50 mg of Compound A is combined with sufficient finely divided lactose to provide a total amount of 580 to 590 mg to fill a size 0 hard gelatin capsule.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula:

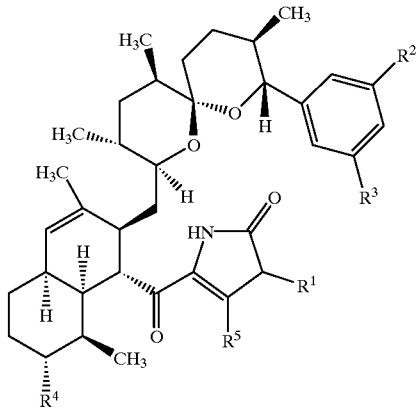

wherein

R$^1$ is —OH, —OCH$_3$, or

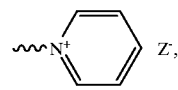

wherein Z$^-$ is a counterion; each of R$^2$, R$^3$, and R$^4$ is independently —OH or —OC(O)CH$_3$; and R$^5$ is (i) —OH when R$^1$ is —OH or —OCH$_3$ or (ii) —OC(O)CH$_3$ when R$^1$ is

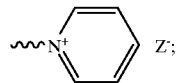

or a pharmaceutically acceptable salt thereof.

2. The compound according to claim 1, which is (a)

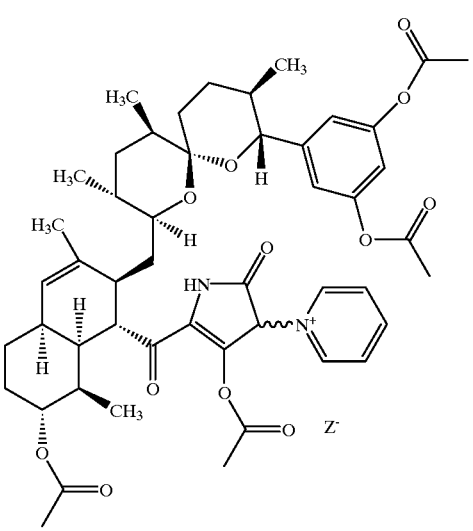

-continued (b)
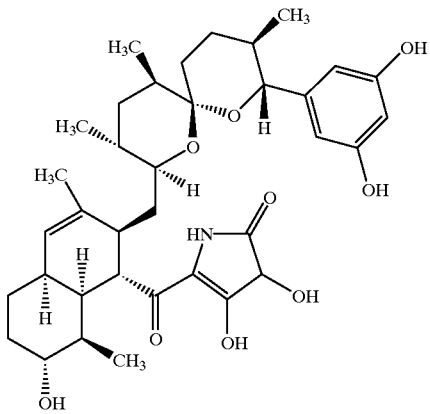

(c)
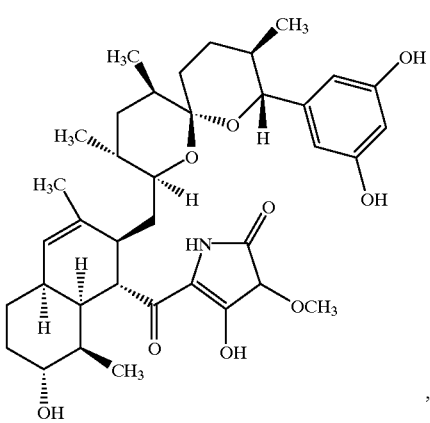

or (d) a pharmaceutically acceptable salt of (a), (b) or (c).

3. The compound according to claim 2, which is

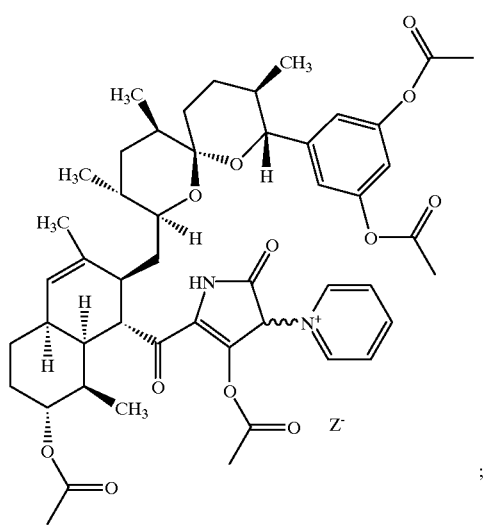

or a pharmaceutically acceptable salt thereof.

4. The compound according to claim 2, which is

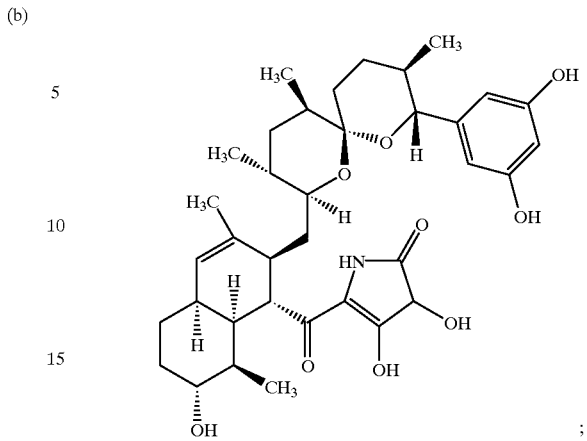

or a pharmaceutically acceptable salt thereof.

5. The compound according to claim 2, which is

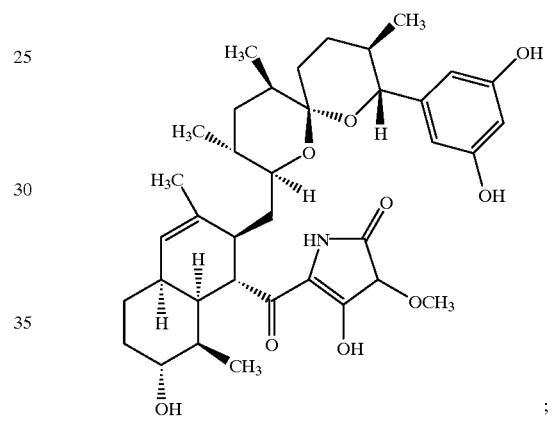

or a pharmaceutically acceptable salt thereof.

6. A pharmaceutical composition comprising a therapeutically effective amount of a compound according to claim 1 and a pharmaceutically acceptable carrier.

7. The pharmaceutical composition of claim 6, further comprising a therapeutically effective amount of an AIDS treatment agent selected from (a) an AIDS antiviral agent, (b) an immunomodulator, and (c) an anti-infective agent.

8. The pharmaceutical composition according to claim 7 wherein the AIDS antiviral agent is indinavir, or a pharmaceutically acceptable salt thereof.

9. A pharmaceutical composition comprising a combination of a therapeutically effective amount of a compound of claim 1 and a therapeutically effective amount of an AIDS treatment agent selected from (a) an AIDS antiviral agent, (b) an immunomodulator, and (c) an anti-infective agent.

10. A process for making a pharmaceutical composition which comprises combining a compound of claim 1 and a pharmaceutically acceptable carrier.

* * * * *